US 9,758,268 B2

United States Patent
Lindgren et al.

(10) Patent No.: US 9,758,268 B2
(45) Date of Patent: Sep. 12, 2017

(54) METHOD AND DEVICE FOR STERILIZING PACKAGING MATERIAL

(71) Applicant: TETRA LAVAL HOLDINGS & FINANCE S.A., Pully (CH)

(72) Inventors: Roger Lindgren, Sovde (SE); Hakan Mellbin, Horby (SE); Jonas Dickner, Paarp (SE); Fredrik Hansen, Bjarred (SE)

(73) Assignee: TETRA LAVAL HOLDINGS & FINANCE S.A., Pully (CH)

( * ) Notice: Subject to any disclaimer, the term of this patent is extended or adjusted under 35 U.S.C. 154(b) by 0 days.

(21) Appl. No.: 14/901,349

(22) PCT Filed: Jun. 19, 2014

(86) PCT No.: PCT/EP2014/062960
§ 371 (c)(1),
(2) Date: Dec. 28, 2015

(87) PCT Pub. No.: WO2014/206861
PCT Pub. Date: Dec. 31, 2014

(65) Prior Publication Data
US 2016/0152365 A1    Jun. 2, 2016

(30) Foreign Application Priority Data

Jun. 25, 2013  (SE) ...................................... 1350773
Jan. 31, 2014  (SE) ...................................... 1450100

(51) Int. Cl.
*A61L 2/00*    (2006.01)
*B01J 19/08*    (2006.01)
(Continued)

(52) U.S. Cl.
CPC .............. *B65B 55/16* (2013.01); *A61L 2/087* (2013.01); *A61L 2/14* (2013.01); *B65B 55/08* (2013.01);
(Continued)

(58) Field of Classification Search
CPC .............................. A61L 2/00; B67C 7/0073
(Continued)

(56) References Cited

U.S. PATENT DOCUMENTS

2010/0054987 A1    3/2010   Krueger et al.
2011/0012032 A1*   1/2011   Bufano ................... A61L 2/087
                                                250/492.3
2012/0219455 A1    8/2012   Meinzinger et al.

FOREIGN PATENT DOCUMENTS

CN    101658683 A    3/2010
CN    102673837 A    9/2012
(Continued)

OTHER PUBLICATIONS

International Search Report (PCT/ISA/210) mailed on Aug. 11, 2014, by the European Patent Office as the International Searching Authority for International Application No. PCT/EP2014/062960.

*Primary Examiner* — Monzer R Chorbaji
(74) *Attorney, Agent, or Firm* — Buchanan Ingersoll & Rooney PC

(57) ABSTRACT

The invention relates to a method for sterilizing packaging material, comprising an emitter that is adapted to emit charge carriers, in particular electrons, wherein the charge carriers form at least one cloud, and wherein the emitter and the packaging material are moved relative to each other so that a flow of a gaseous medium is established in between the emitter and the packaging material. The method comprises the steps of: controlling a movement profile between the emitter and the packaging material; sterilizing the flow of the medium in between the emitter and the packaging (Continued)

Figure 1:
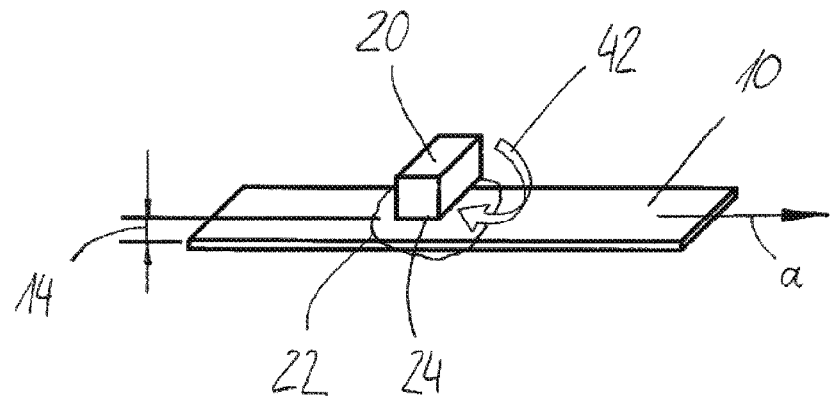

material by adjusting the movement profile so that the flow of the medium in between the emitter and the packaging material is sterilized. Also disclosed is a device for sterilizing packaging material.

17 Claims, 6 Drawing Sheets

(51) Int. Cl.
*A61N 5/00* (2006.01)
*B65B 55/16* (2006.01)
*A61L 2/08* (2006.01)
*B65B 55/08* (2006.01)
*A61L 2/14* (2006.01)
*G21K 5/10* (2006.01)

(52) U.S. Cl.
CPC ............. *G21K 5/10* (2013.01); *A61L 2202/11* (2013.01); *A61L 2202/14* (2013.01)

(58) Field of Classification Search
USPC ....... 422/1, 3, 22, 119, 186; 250/492.3, 395, 250/397
See application file for complete search history.

(56) References Cited

FOREIGN PATENT DOCUMENTS

| | | | |
|---|---|---|---|
| CN | 103157121 | A | 6/2013 |
| WO | 2007145561 | A1 | 12/2007 |
| WO | 2014095838 | A1 | 6/2014 |

* cited by examiner

METHOD AND DEVICE FOR STERILIZING PACKAGING MATERIAL

This invention relates to a method for sterilizing packaging material and to a device for sterilizing packaging material.

In the prior art different devices and methods for sterilizing packaging materials are known. One method widely used in the prior art is sterilization by means of gases and in particular by means of hydrogen peroxide. However, efforts are being made to reduce the use of chemicals when sterilizing containers. Therefore, devices and methods have also become known which sterilize material by means of ultra-violet radiation or electron beams. In general for electron beams, there is provided an emitter that is adapted to emit charge carriers, in particular electrons, wherein the packaging material can be sterilized by these charge carriers. For this purpose the packaging material and the emitter, respectively, are moved relative to each other, e.g. an electron gun is put into a bottle-shaped package. However, when the emitter and the packaging material are moved relative to each other, flows or streams of a medium, such as air, are established in between. If these streams or flows comprise a medium, such as air, that is not sterile or aseptic, there exists the risk that parts of the packaging material that have already been sterilized are re-infected by the unsterile or non-aseptic air-streams or -flows.

Therefore, it is an object of the current invention to provide a method for sterilizing packaging material and a device for sterilizing packaging material to maintain aseptic conditions on a packaging material during and after the sterilization.

This object is achieved by a method for sterilizing packaging material according to claim 1 and by means of a device according to claim 13. Additional advantages and features of the embodiments of the current invention are defined in the dependent claims.

According to the invention, the method for sterilizing packaging material comprises an emitter that is adapted to emit charge carriers, in particular electrons, wherein the charge carriers form at least one cloud, and wherein the emitter and the packaging material are moved relative to each other so that a flow of a gaseous medium is established in between the emitter and the packaging material, the method further comprises the steps of:
  controlling a movement profile between the emitter and the packaging material;
  sterilizing, by the at least one cloud, the flow of the gaseous medium in between the emitter and the packaging material by adjusting the movement profile.

Actually, the flow of the medium in between the emitter and the packaging material is usually established in a gap that is established in between the emitter and the packaging material. The gap can have a constant size or thickness, when the packaging material is for example flat. However, the gap does not have to be constant, its size can change, respectively, when the emitter and the packaging material are moved relative to each other. This means that the gap can get thicker and/or thinner when the emitter and the packaging material are moved relative to each other. The speed of the flow of the gaseous medium in the gap depends on the size/thickness of the gap and the speed of the relative movement. The speed of the medium is the faster the smaller the gap is and/or the quicker the relative movement is. The object of the invention is to sterilise the flow of the gaseous medium in the gap by the cloud of electrons from the emitter.

However, if the speed of the flow of the gaseous medium in the gap is too fast, the time is too short to sterilize the medium. This means that the medium that has passed the cloud is not sterilized. According to the invention, the flow of the medium in between the packaging material and the emitter is controlled by adjusting the movement profile. In other words, the flow of the medium is controlled in a way so that the flow of the medium in between the emitter and the packaging material is sterilized. Especially, the speed of the medium in the gap is controlled via the movement profile. The speed of the medium should be slow enough to allow sterilization time when it passes the electron cloud. The speed of the medium depends on the size of the gap and the movement profile in between the emitter and the packaging material or on a relative speed in between the emitter and the packaging material, respectively. The smaller the relative speed between the emitter and the packaging material is, the smaller is the speed of the flow of the medium.

The movement profile is adapted to control the speed of the flow of the medium in the gap so that sterilization of the flow of the medium can be realized. For this purpose, the cloud of electrons is adapted to cover preferably the complete gap. This ensures that the entire flow of the medium that passes the gap is sterilized, i.e. that all the medium flowing in through the gap is sterilized. The cloud forms an aseptic barrier when the emitter is extracted. The present method makes it possible to maintain aseptic conditions in the packaging material during and after the sterilization. In other words, it can be made sure that any gaseous medium that comes into contact with the (sterilized) packaging material is sterile.

The movement profile can be adapted to every gap size. This means that the packaging material can have any form or geometry. According to the "medium" it has to be mentioned that the medium is not specifically constrained concerning its mixture. It may be for example air or nitrogen or any other gas or mix of gases. "Medium" means a medium that is may not be sterile. In general a medium is meant something that could re-infect the already sterilized packaging material. Sterilization is a term referring to any process that eliminates or kills microbial life, including transmissible agents such as for example fungi, bacteria, viruses and spores, which may be present on a surface of the packaging material or in a product. In the (food) packaging industry this is generally referred to as aseptic packaging, i.e. packaging sterilized products in sterilized packaging containers, i.e. keeping both the product and the packaging container free form living germs and microorganisms, so that the freshness of the product can be preserved without special cooling requirements, i.e. so that sterility can be maintained inside a packaging container although it is stored in ambient temperature. In this context the term "commercially sterile" is also commonly used and means in general the absence of microorganisms capable of growing in the food at normal non-refrigerated conditions at which the food is likely to be held during manufacture, distribution and storage. In this patent application the word "sterile" refers to a condition being at least commercially sterile.

In one or more embodiments the packaging material is basically tube-shaped, and the emitter is adapted for sterilization of at least the interior of the tube-shaped packaging material through an opening of the tube-shaped packaging material. The opening is adapted to enable an insertion of the emitter into the basically tube-shaped packaging material. The basically tube-shaped packaging material is closed at its other end portion opposite the opening. The tube-shaped packaging material extends along an axis. The term "tube shaped" comprises no limitations concerning the possible form of the cross-section of the basically tube shaped packaging material. This means that the cross section can be round, rectangular, circular, polygonal and/or angular and especially, the cross section of the basically tube shaped packaging material does not have to be constant along the axis. Without limiting the generality the basically tube-shaped packaging material is sometimes named "packaging container" in the following.

The packaging container can for example be made of a plastic material such as for instance PET, or be made of a (laminated) carton material. With regard to the later a common type of laminated carton material is the ones comprising a core layer of paper or paperboard and one or more barrier layers of, for example, polymer material or aluminium foil. An increasingly common packaging type is the "carton bottle" manufactured in a filling machine in that packaging blanks of the above-described packaging laminate are formed and sealed as a sleeve. Said sleeve is closed in one end in that a top of thermoplastic material is injection moulded directly on the sleeve end portion. The sheets of packaging laminate may be cut from a magazine reel of packaging laminate.

Advantageously, the opening of the packaging container, e.g. the spout or a bottom of the packaging container, has to be big enough so that at least the portion of the emitter comprising the electron exit window can be passed through it, to sterilize in particular the interior surface of the packaging container. In one or more embodiments the emitter has a round, in particular a circular cross section that is basically constant. A diameter of the cross-section lies within a range of about 5-100 mm.

In one or more embodiments the method comprises the step of:
   performing a mutual relative movement between the emitter and the tube-shaped packaging material, during which movement a portion of the emitter is temporarily inserted through the opening of the tube-shaped packaging material, such that interior sterilization of the packaging material takes place.

The term "relative movement between the emitter and the tube-shaped packaging material" comprises every possible movement arrangement. In one or more embodiments the emitter moves in relation to the packaging container (the packaging container being stationary along the axis). Alternatively, in one or more embodiments the packaging container moves towards and away from the emitter (the emitter being stationary along the axis). The emitter will hence be inserted into the packaging container in that the emitter is received in the packaging container. In other words, the packaging container will be moved to surround the emitter. Alternatively, in one or more embodiments, both the emitter and the packaging container are moved. Each performs a part of the relative movement.

Inserting the emitter into the basically tube-shaped packaging material creates basically an outflow of the medium out of the basically tube-shaped packaging material through the opening wherein pulling the emitter out of the basically tube-shaped packaging material creates basically an inflow of the medium into the basically tube-shaped packaging material. The method comprises the step of:
   adapting an inflow-speed and an outflow-speed of the medium using the movement profile.

For the sake of completeness, to avoid ambiguity, it is to be understood that the term "inserting" and pulling out" refers to a relative movement. Hence, "inserting" includes any movement of the emitter and the packaging container towards each other. Correspondingly, the term "pulling out" includes any movement of the emitter and the packaging container away from each other.

Pulling the emitter out of the basically tube-shaped packaging material creates basically an inflow of the medium into the basically tube-shaped packaging material. The method comprises the step of:
   adapting an inflow-speed of the medium, using the movement profile, such that the inflow of the medium into the basically tube-shaped packaging material is sterilized by the cloud. In other words, the medium flowing into the packaging container is sterilized by the cloud.

The aforementioned inflow is created in the same way when the emitter does not move and the packaging material is moved away from the emitter. In the same way, the outflow is created when the emitter does not move and the packaging container is moved towards (and pulled over) the emitter. In one or more embodiments the inflow-speed as well as the outflow-speed of the medium can be decelerated by decelerating the relative movement speed between the emitter and the packaging material. In one or more embodiments, the side of the packaging container opposite the opening (through which the emitter is inserted) is preferably closed. This means that the medium or the air, respectively, that is inside the packaging container, when the emitter is inserted into the container is pushed out of the container creating the outflow of the medium. Similar to this, air or medium, respectively, around the packaging container is sucked into the packaging container via the opening or the gap, respectively, when the emitter is pulled out from the packaging container. This means that un-purified, non-aseptic or non-sterile medium/air could come into the container if the flow of the medium via the gap is not sterilized by the cloud. However, advantageously the movement profile is adapted in a way so that the flow of the medium that comes into the packaging container is slow enough so it can be sterilized by the emitter while passing the cloud of the emitter.

In one or more embodiments the movement profile comprises at least a first position, wherein at the first position the emitter, in particular its electron exit window, and the opening of the basically tube shaped packaging material are basically on the same level, and a second position, wherein at the second position the emitter, in particular its electron exit window, is located inside the basically tube shaped packaging material, the method comprises the step of:
   adjusting the movement profile so that a time span for moving from the first position to the second position, defined as run-in, is shorter than a time span for moving from the second position to the first position, defined as run-out.

Naturally, in for example a filling machine, there is only a certain span of time available for the sterilization of the inner part of the packaging container. In one or more embodiments a plurality of emitters are provided on a carousel or the like which is adapted to rotate (the basic arrangement is known from the prior art). Expediently, the packaging containers which are transported for example via a conveyor reach the carousel and are attached to one of the (rotating) emitters. During at least a part of one rotation of the carousel, the sterilization takes place and the packaging container is removed from the appropriate emitter or from the carousel, respectively. Therefore, dependent on the size of the carousel, the number of the emitters arranged at the carousel and/or the rotation speed of the carousel a certain span of time for sterilization is available. If having a non-sterile emitter and if the carousel is arranged in a non-aseptic chamber, the sterilization is preferably made during the run-out of the packaging container. The cloud will itself form an aseptic barrier in the packaging container. During run-in the emitter will be in operation, however the actual sterilization will start when the cloud fills the closed end of the packaging container, i.e. when the cloud is positioned farthest away from the opening. As the emitter is pulled out of the packaging container the aseptic barrier is moved upwards, towards the opening.

To allow for sufficient time for run-out, to control the speed of the in-flow, the time for run-in is adjusted to be shorter than the time span for run-out. If the time span for run-out is longer, the available time span for sterilization the inside of the packaging material during run-out is longer and the inflow can be adjusted so that it can be sterilized by the cloud, i.e. such that any medium flowing in can be sterilized.

Making the time span for run-out as long as possible, the medium flowing in via the gap can be sterilized by the cloud because it is as slow as possible. It goes without saying that the run-out does not stop at the first position. The opening of the packaging container is only a reference point that was chosen to describe the movement profile. The second position is preferably a deepest position of the emitter, in particular its electron exit window, inside the packaging container. Of course, the second position is located preferably so deep inside the packaging container that the cloud can reach the whole inside of the side of the packaging container, which is opposite to the entry side, i.e. the opening. As a consequence, the second position depends on the length of the packaging material or container and on the size of the cloud. In one embodiment, a distance between the first and the second position measures about 10 and 400 mm. The available time span for sterilization, in other words the time span for run-in and run-out measures about 0.1-10 s in total.

In one or more embodiments the method comprises the steps of:
adjusting the time for run-out to be at least 5-times as long as the time for run-in;
sterilizing the basically tube-shaped packaging material during run-out.

In one or more embodiments the time for run-out is at least 8-times as long as the time for run-in, especially preferred the time for run-out is at least 10-times as long as the time for run-in. As a consequence, the time for sterilizing the packaging material during run-out can be increased.

The tube-shaped packaging material extends basically along an axis, the cloud comprises a width that extends basically perpendicular to the axis, and the cloud comprises a length that extends basically along the axis. In one or more embodiments the method comprises the steps of:
providing a power supply, wherein the power supply is adapted to influence the width and the length of the cloud;
forming the width so that it is adapted to cover at least the area between the emitter and the packaging material.

This means that the cloud is adapted to cover preferably the entire gap. Also preferably, the cloud or the width of the cloud, respectively, is also adapted to cover the diameter of the opening. Generally, the gap measures about 1 to 50 mm. Obviously, the emitter diameter should be less than the diameter of the packaging container, to provide for a gap, and thereby easy movement of the emitter and the packaging material relative to each other. Expediently, the place in between the emitter and the surrounding packaging material or the gap, respectively, is covered completely by the cloud. In other words, the gap is completely closed by the cloud so that the entire medium that passes the gap has to pass the cloud. As a consequence, it can be easily reacted on different gap sizes by adjusting the width of the cloud. In combination with controlling the movement profile between the packaging material/container and the emitter it can be ensured that the inflow of non-sterile/non-aseptic air/medium, i.e. the medium flowing in, is always sterilized, independent of the form of the packaging material. In addition, the power supply is adapted to control that the inside of the packaging container is not overexposed to the electrons, i.e. that the output dose rate of the emitter is not too high.

In one or more embodiments, the method comprises the step of:
adapting the energy level of the charge carriers and/or the dose rate of the emitter as a function of the flow-speed of the medium in between the emitter and the packaging material.

In particular, the energy level of the charge carriers and/or the output dose rate of the emitter, respectively, is adapted as a function of the inflow-speed of the medium in between the emitter and the packaging material, at least during run-out.

The idea is to align the energy level of the charge carriers and/or the output dose rate, respectively, to the speed of the medium, in particular the speed of the inflow of the medium. This means, the energy level of the charge carriers and/or output dose rate, respectively, should be the higher, the higher the flow-speed, in particular the inflow-speed is. This can ensure sufficient sterilization of the inflow. In one or more embodiments the energy level of the charge carriers and/or the output dose rate of the emitter, respectively, are not constant during the entire movement profile. Expediently, the energy level is increased during run-out to ensure sterilization of the inflow of the medium, i.e. sterilization of the medium flowing in. It goes without saying that adjusting the energy level of the electrons and/or the output dose rate of the emitter is preferably combined with adjusting the movement profile itself.

In one or more embodiments the method comprises the step of:
adapting the length and/or the width of the cloud during run-out when the emitter is outside the packaging material to cover the opening of the packaging material with the cloud.

The speed of the medium or the gas, such as air, respectively, depends not only on the size of the gap when the emitter is positioned within the packaging material. There is also an inflow of the medium when the emitter is already outside the packaging material. This is based on the inertia of the flow of the medium. In other words, the inflow after pulling the emitter out of the packaging container still exists when the emitter is already above the aforementioned first position. This means that the speed of the inflow of the medium depends also on the speed of the emitter when leaving the packaging material. In one or more embodiments, the length and/or the width of the cloud are increased when the emitter is outside the packaging material during run-out, in other words, when the emitter is slightly above the opening of the packaging container (first position). Preferably, the cloud is adapted so that the inflow is sterilized by the cloud. The cloud should have a width w larger than the opening of the packaging container to ensure sterility of the inflow.

In one or more embodiments the method comprises the steps of:
lowering and/or stopping the run-out speed when the emitter is above the opening;

adapting the cloud being big enough to cover at least temporarily the opening;
sterilizing the inflow of the medium.

This means that the movement profile in between the packaging container and the emitter is preferably adjusted so that the relative speed between the packaging material and the emitter is lower, decreased or stopped, respectively, when the emitter is above the opening. This makes sure that an inflow that is sucked into the packaging container after the emitter has been pulled out of the container is also sterilized.

In one or more embodiments the method comprises the step of:
providing a drive unit to enable the movement profile by moving the packaging material along the axis.

In one or more embodiments the drive unit comprises any of the following: a linear motor, a servo motor, a pneumatic drive/motor or a mechanical drive such as for example a cam curve. Alternatively, also a standard (rotating) electric motor can be used, wherein a mechanism is provided that translates the rotation in a stroke move. In one or more embodiments a linear motor is used. The linear motor has a minimum stroke that enables the aforementioned distances between the first and the second position and even longer distances (as in the first position the emitter is only on the level of the opening of the packaging container).

In one or more embodiments the method comprises the step of:
pre-loading a drive mechanism of the linear motor using a pre-load device to improve a speed of the motor.

As already mentioned, it is preferred to shorten the time for run-in. As a consequence, for moving the packaging container or the emitter, a motor has to be provided that is very strong to enable the appropriate accelerations. To enable the usage of smaller and as a consequence also cheaper electric motors the drive mechanism of the electric motor can be combined with a pre-load device as for example a spring or a rubber element that can be used to support the movement of the drive mechanism or the electric motor, respectively. In other words, the preload device can be compresses or the like and the stored energy can be used to support the possible accelerations of the electric motor.

In one or more embodiments the method comprises the steps of:
creating overpressure inside the basically tube-shaped packaging material to prevent the inflow coming into the basically tube-shaped packaging material.

In one or more embodiments the emitter comprises at least one outlet or the like to create a condition inside the packaging container that prevents medium from outside from coming into the container. A pressure inside the container is bigger than a pressure outside the container. It could be also possible to generate an outflow of e.g. sterile air out of the container that stops the inflow that exists during pullout of the emitter.

According to the invention, there is also provided a device for sterilizing packaging material, comprising an emitter that is adapted to emit charge carriers, in particular electrons, wherein the charge carriers form at least one cloud, and wherein the emitter and the packaging material are moved relative to each other so that a flow of a gaseous medium is established in between the emitter and the packaging material, wherein the devise comprises a control unit that is adapted to control a movement profile in between the emitter and the packaging material, wherein the flow of the medium in between the emitter and the packaging material can be sterilized by adjusting the movement profile.

The device according to the invention can include the features and advantages of the methods according to the invention and vice versa.

Additional advantages and features of the current invention are shown in the following description of embodiments of the current invention with reference to the attached drawings. Single features or characteristics of respective embodiments are explicitly allowed to be combined within the scope of the current invention.

Figure 2A:
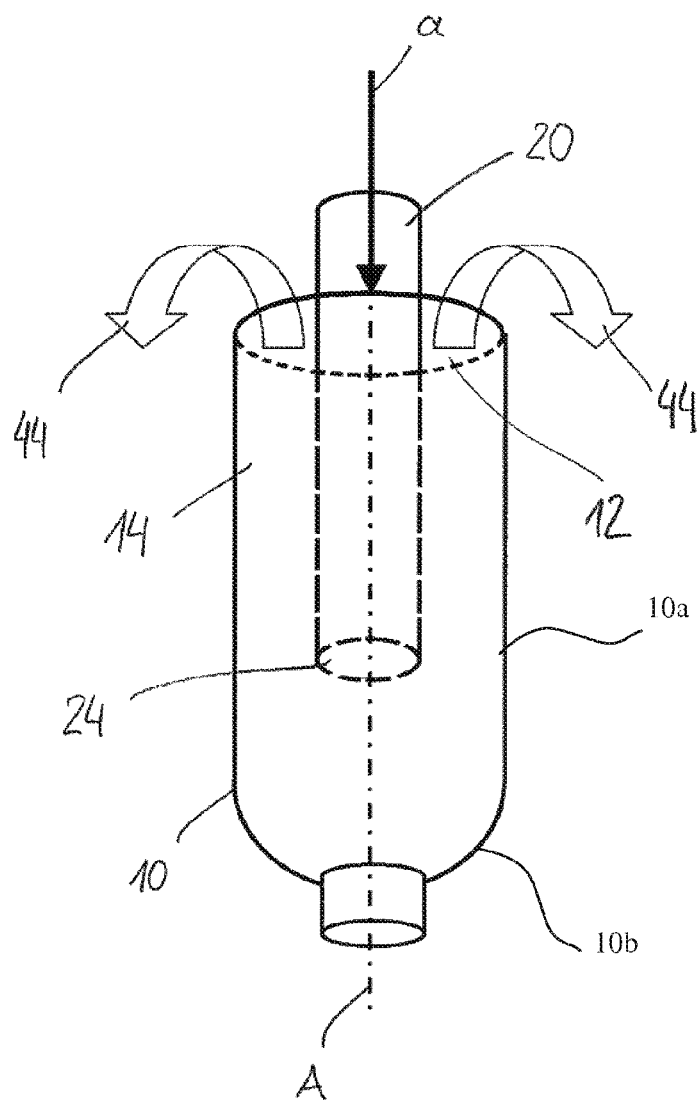
Figure 3:
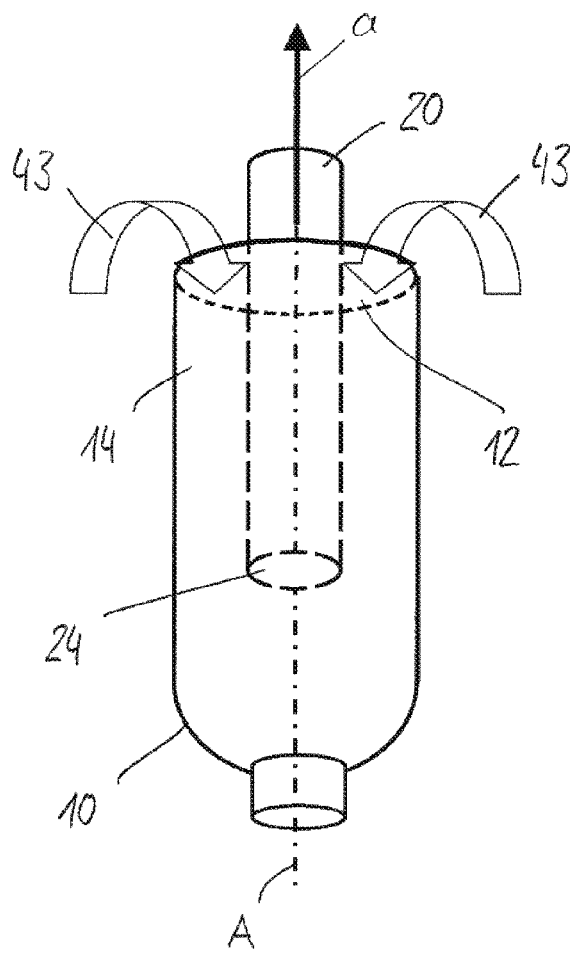
Figure 2B:
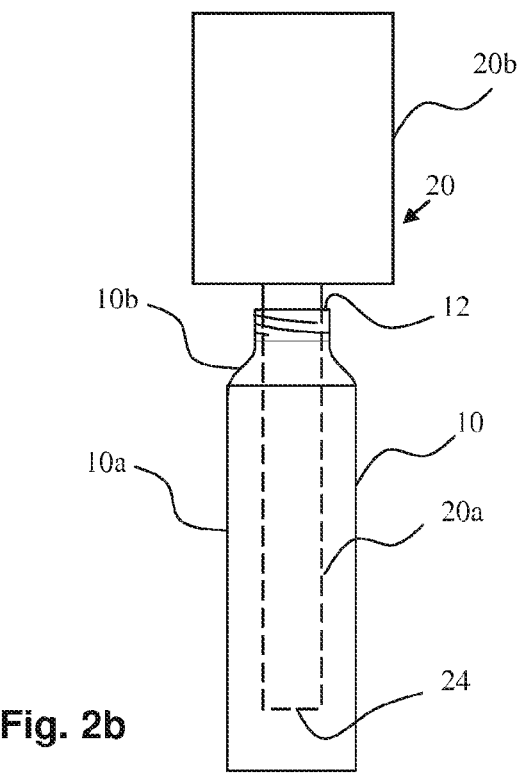
Figure 4:
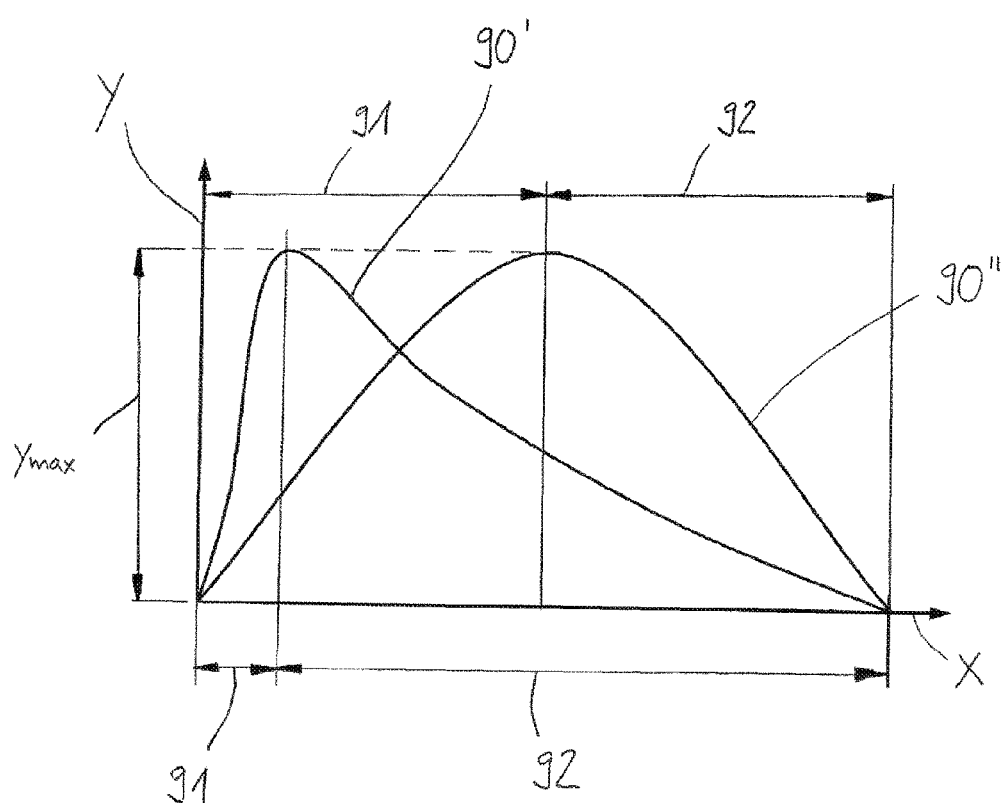
Figure 5:
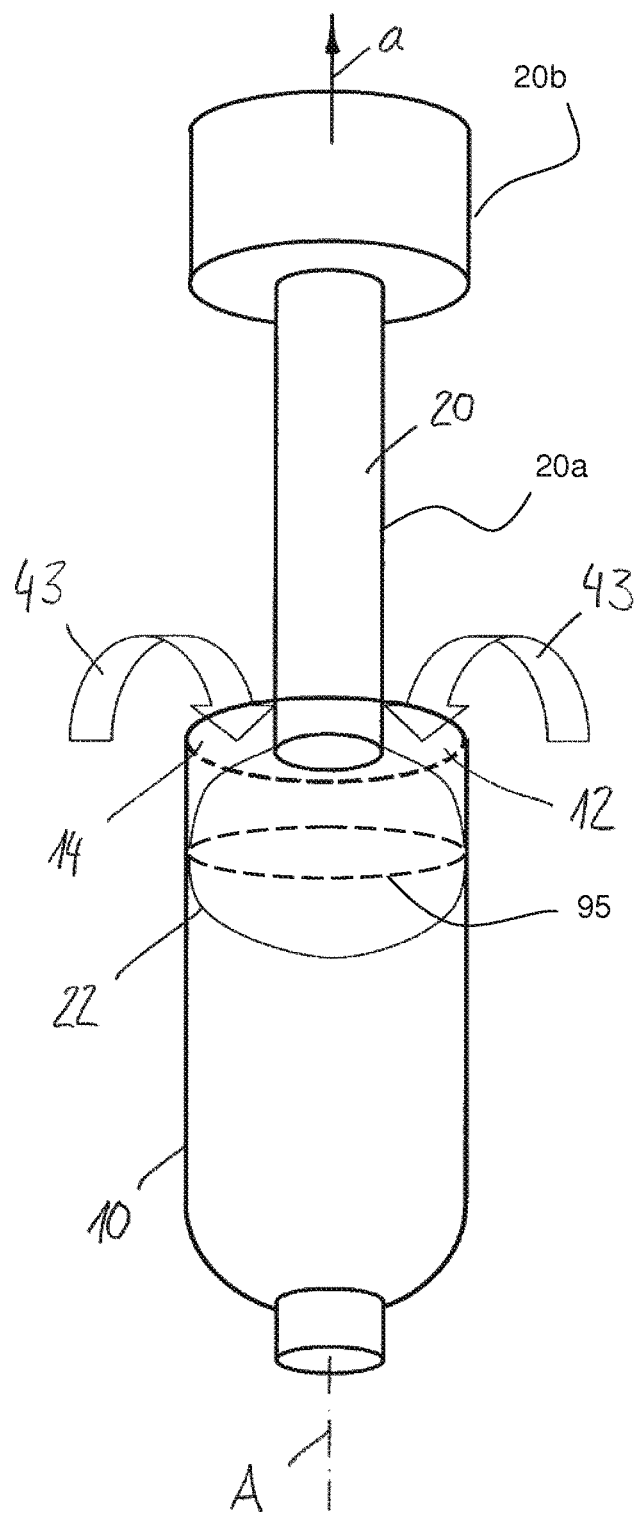
Figure 6:
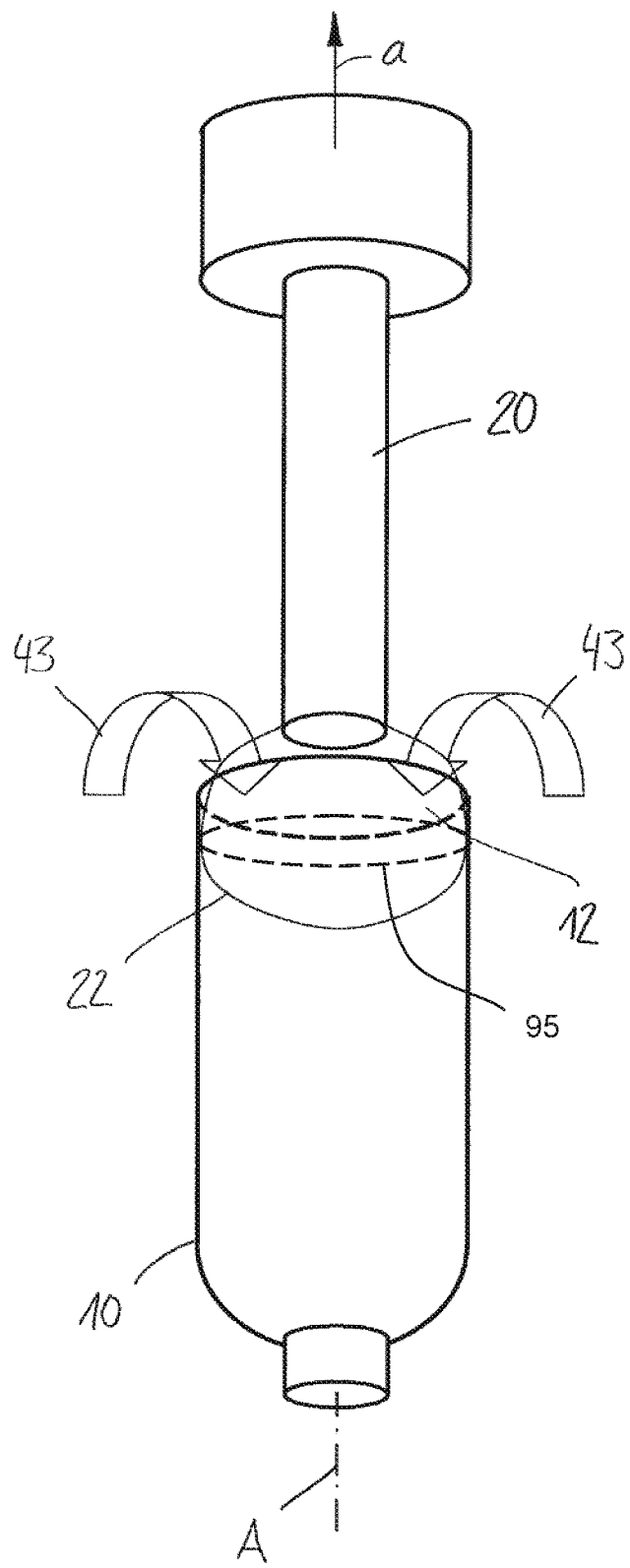
Figure 7:
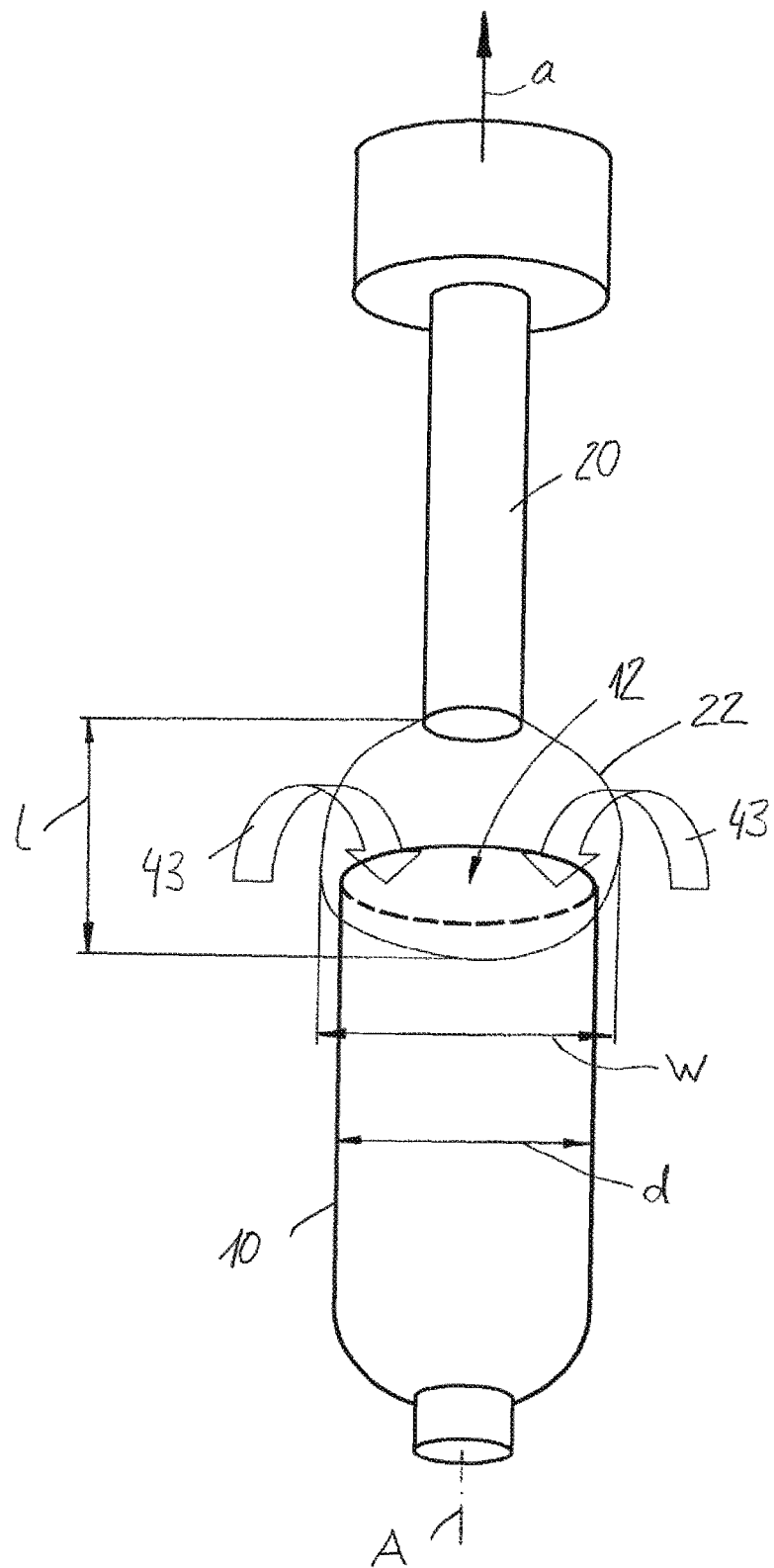

FIG. 1: shows schematically a flow of a medium between an emitter and a packaging material that move relative to each other;

FIG. 2a: shows schematically an outflow of a medium when an emitter is inserted into a basically tube-shaped packaging material;

FIG. 2b: shows schematically an alternative packaging container and an emitter;

FIG. 3: shows schematically an inflow of a medium into a basically tube-shaped packaging material when an emitter is pulled out of the basically tube-shaped packaging material;

FIG. 4: shows two movement profiles;

FIG. 5: shows schematically how an inflow can be sterilized by a cloud of an emitter;

FIG. 6: shows a sterilization of an inflow of a medium when an emitter is already pulled out of a basically tube-shaped packaging material;

FIG. 7: shows an adaption of a cloud to sterilize an inflow into a basically tube-shaped packaging material.

Referring now to FIG. 1, a packaging material 10 is shown that is moved along a direction of an arrow a. An emitter 20 is positioned so that a gap 14 is formed between the emitter 20 and the packaging material 10, wherein the emitter 20 comprises an electron exit window 24. The electron exit window 24 faces down towards the packaging material. The gap 14 is covered by a cloud 22 that is formed by charge carriers, in particular electrons, that are emitted by the emitter. The movement of the packaging material 10 relative to the emitter 20, which does not move, establishes a flow 42 of a medium in between the emitter 20 and the packaging material 10 or in between the emitter 20 and the packaging material 10, respectively. As FIG. 1 shows, the direction of the flow 42 of the medium is directed basically opposite the arrow a. The relative movement in between the emitter 20 and the packaging material 10 or a movement profile, respectively, is adapted or adjusted so that the flow 22 of the medium in between the emitter 20 and the packaging material 10 is sufficiently sterilized by the cloud 22.

FIG. 2a shows an embodiment of an emitter 20 that is inserted into a basically tube-shaped packaging material 10. In particular, the basically tube-shaped packaging material 10 is a packaging container in a shape ready to be filled with product through an opening 12. It comprises a sleeve body 10a and a top portion 10b. The top portion 10b comprises a neck or spout sealed with a closure. The closure can for example be a screw cap, flip-cap (hinged cap) or membrane. The sleeve body 10a is provided with the opening 12.

In this embodiment the opening 12 of the packaging container 10 is an open bottom end, which after filling will be sealed and folded to form a substantially flat bottom surface. It should however be understood that this opening 12, through which the emitter 20 is received and through which filling will be made, may in other embodiments be arranged in the top portion 10b of the packaging container, as a neck or spout portion of the packaging container 10.

FIG. 2b illustrates such embodiment. The neck or spout portion will, after filling, be sealed by for instance a screw cap.

In FIG. 2a it is seen that the packaging container extends along an axis A. The emitter 20, which also extends along the axis A, is inserted into the packaging container 10 along an arrow a. In between the packaging container 10 and the emitter 20 a gap 14 is formed. The emitter 20 comprises an exit window 24 that is adapted to emit charge carriers, in particular electrons. During inserting the emitter 20 into the packaging container 10 an outflow 44 of a medium inside the packaging container 10 is established in the gap 14 wherein the outflow 44 exits the inside of the packaging container 10 via the opening 12.

In the following an exemplary emitter 20 for sterilizing the interior of this ready-to-fill packaging container 10 will be briefly described.

The emitter 20 comprises an electron generator for emitting a substantially circular electron beam along a path. The electron generator 14 is enclosed in a hermetically sealed vacuum chamber. Said vacuum chamber is provided with an electron exit window 24.

The electron generator comprises a cathode housing and a filament. In use, an electron beam is generated by heating the filament. When an electrical current is fed through the filament, the electrical resistance of the filament causes the filament to be heated to a temperature in the order of 2000° C. This heating causes the filament to emit a cloud of electrons. The electrons are accelerated towards the electron exit window 24 by means of a high-voltage potential between the cathode housing and the exit window (being the anode). Subsequently, the electrons pass through the electron exit window 24 and continue towards the target area, i.e. in this case the interior surface of the packaging container 10.

The filament can be made of tungsten. A grid may optionally be placed between the filament and an electron beam exit window. The grid may be used for diffusing the electron beam into a more uniform beam, and for focusing the electron beam towards the target area.

The high-voltage potential is created by for example connecting the cathode housing and the filament to a power supply and by connecting the vacuum chamber to ground. The emitter 20 is generally denoted low voltage electron beam emitter if the voltage is below 300 kV. In one or more embodiments the accelerating voltage is in the order of 90-110 kV. In one or more embodiments the voltage is 100 kV. This voltage results in a kinetic (motive) energy of 100 keV in respect of each electron. However, another voltage can be chosen, for example in the interval 75-150 kV.

The emitter 20 is, as mentioned, further provided with an electron exit window 24. The window 24 can be made of a metallic foil, such as for example titanium, and can have a thickness in the order of 4-12 µm. A supporting net (not shown) formed of aluminum or copper supports the foil from inside the vacuum chamber. The electrons are exiting the vacuum chamber through the exit window 24.

The vacuum chamber may, as shown in for example FIG. 2b or 5, be made up of two elongate cylindrical bodies 20a, 20b with substantially circular cross sections. The cylindrical bodies have a common longitudinal centre axis A. The first cylindrical body 20a has an end surface, in a plane being perpendicular to the centre axis A, being provided with the electron exit window 24. The electron exit window 24 is circular and preferably extends over most of the end surface. The diameter of said first body 20a is small enough to be inserted into the ready-to-fill packaging container 10, the cross section of said first body is dimensioned such that it can be guided through the opening 26 of the packaging container 10. The second body 20b is provided with the electron beam generator, and the diameter of said second body 20b is larger than the first body 20a.

The emitter 20 emits, from its electron exit window 24, an electron cloud 22 illustrated schematically by a line in for example FIG. 5. The cross sectional shape is somewhat circular, as shown, or droplet-shaped. The shape of the electron cloud is defined by the shape of the electron exit window 24 and by the Brownian motion of individual electrons leaving the electron exit window. When leaving the electron exit window and enter into air the electrons will scatter in all directions forming a cloud. The cloud formed is basically axis-symmetrical, around axis A, and the cloud volume is thereby spherical (or droplet-shaped). To obtain sterilization of the interior surface of the packaging container the energy of the emitter 20 needs to be matched with the sterilization time available, the packaging container size and shape and the packaging container velocity relative the emitter.

FIG. 3 shows basically the same embodiment as FIG. 4. However, the emitter 20 is pulled out of the packaging container 10 along the arrow a. This establishes an inflow 43 that is directed into the packaging container 10 via the opening 12 and the gap 14 which is established in between the packaging container 10 and the emitter 20. It goes without saying that this effect is the same when the packaging container 10 is moved against the arrow a and the emitter 20 is stationary, i.e. when the emitter does not move along the arrow a (that applies also to the movement in FIG. 2a).

As previously mentioned the emitter and the tube-shaped packaging container are adapted to perform a relative movement. Although the emitter is in operation (emitting a cloud) during the entire relative movement, the actual sterilization of the interior of the tube-shaped packaging material is considered to be made when the emitter is pulled out of the tube-shaped packaging material. In such case the emitter itself does not need to be sterile and the cloud forms an aseptic barrier between the sterilized interior surface and the emitter. Such aseptic barrier can be maintained as long as the inflow 43 of gaseous medium can be controlled such that it is secured that it is sterilized by the cloud. In other words, any inflow 43 of gaseous medium should be sterilized in the cloud before being able to cross the aseptic barrier and reach inside the sterilized tube-shaped packaging material. This will be further described in relation to FIGS. 4 and 5.

FIG. 4 shows two movement profiles 90' and 90" in a diagram. The x-axis x of the diagram shows the time, e.g. in ms. The y-axis y shows a lift or a distance, e.g. in mm, respectively. The lift refers to a first and a second position, wherein at the first position an emitter 10, in particular its electron exit window 24, and an opening 12 of the packaging container 10 are basically on the same level, and wherein at the second position the emitter 20, in particular its electron exit window 24, is located inside the packaging container, as for example shown in FIG. 2a. The second position is adjusted so that the entire inside of the packaging container 10 can be sterilized by the cloud 22 of electrons. This means that the second position has to be so deep inside the packaging container 10 so that the cloud can reach the inside of the packaging container 10 sufficiently. The movement profile 90' shows a time span for run-in 91 that is much shorter than a time span for run-out 92. In one or more embodiments the time span for run-in 92 measures about 150 ms, wherein the time span for run-out 92 measures about 1350 ms. Contrary to this, the movement profile 90" shows that a time span for run-in 91 is basically as long as a time span for run-out 92.

In the case of non-sterile emitters, the movement profile 90' is the preferred one. The emitter may then enter the tube-shaped packaging container quickly causing a quick outflow 44 (FIG. 2*a*). Alternatively, the tube-shaped packaging material is quickly raised to surround the emitter. Sterilization of the interior surface of the tube-shaped packaging material "starts" when the cloud fills the top portion 10*b* of the tube-shaped packaging material. The emitter can then be slowly retracted from the packaging material, or alternatively, the packaging material can be slowly moved away from the emitter. The cloud will form an aseptic barrier that, during the relative movement, will be displaced towards the opening 12 in the tube-shaped packaging material, leaving a sterile interior surface in the packaging material underneath the cloud. The relative slow motion will prevent the inflow 43 of gaseous medium to flow through the cloud without being sterilized. This is further described in FIG. 5.

FIG. 5 shows an embodiment for sterilizing an inflow 43 that is directed into a basically tube-shaped packaging material 10 which extends basically along an axis A by a cloud 22. An emitter 20 is pulled out along an arrow a wherein this pullout establishes the inflow 43 that is directed into the packaging container 10. However, the inflow 43 cannot come into the basically tube-shaped packaging material 10 without passing the cloud 22. The cloud forms an aseptic barrier 95, shown as a plane in dashed line, between the sterilized interior surface of the packaging material and the emitter 20. The speed of the emitter 20 along the arrow a is slow enough so that the inflow 43 is sterilized by the cloud 22.

Of course, as mentioned before, it is also possible to alternatively move the packaging container 10 along the axis A without moving the emitter 20 (emitter being stationary). Alternatively, both the emitter 20 and the packaging container 10 can be moved along the axis A, i.e. the relative movement is performed by both. Advantageously, the movement profile in between the emitter 20 and the basically tube shape packaging material 10, or in general the packaging material 10, is adapted so that the flow 42 of the medium in between the emitter 20 and the packaging material 10 is sterilized.

FIG. 6 shows basically the same embodiment as shown in FIG. 4. However, the emitter 20 is already outside the tube-shaped packaging material 10. Similar to FIG. 5, there may still be an inflow 43 directed into the packaging container 10. The cloud 22 is adapted to sterilize the inflow 43 that comes via the opening 12 into the basically tube-shaped packaging material 10, and the inflow 43 cannot access the area underneath the aseptic barrier 95 without first being sterilised. In one or more embodiments the movement profile is adapted to hold the arrangement as shown in FIG. 6 for a certain time to make sure that the inflow 43 is sterilised by the cloud 22. This means that the relative speed between the packaging material 10 and the emitter 20 can be lowered or also shortly stopped to ensure the sterilization of the inflow 43.

FIG. 7 shows an embodiment that is similar to the ones shown in FIGS. 5 and 6. However, it is shown that a width w and a length l of the cloud 22 are adapted to make sure that the inflow 43 is sterilized. Compared to FIG. 6 it is obvious that the width w of the cloud 22 is bigger than a diameter d of the packaging container 10. The size of the cloud 22 can be adapted using an appropriate power supply to adapt the energy level of the charge carriers and/or its speed or its output dose rate, respectively.

The invention can be applied in for example a sterilization device as described in the international application No. PCT/EP2013/076870 filed by the applicant. During interior sterilization of the packaging containers a relative movement is made between the packaging container and the emitter.

REFERENCE NUMERALS

10 (basically tube shaped) packaging material, packaging container
10*a* sleeve body
10*b* top portion
12 opening
14 gap
20 emitter
20*a* first cylindrical body
20*b* second cylindrical body
22 cloud
24 electron exit window
26 packaging container opening
42 flow
43 inflow
44 outflow
90', 90" movement profiles
91 run-in
92 run-out
95 aseptic barrier
x x-axis
y y-axis
$y_{max}$ maximum lift, distance in between the first and the second position
w width
l length
A axis
a arrow
d diameter of the packaging container

The invention claimed is:

1. Method for sterilizing packaging material through use of an emitter that is to emit charge carriers forming at least one cloud, the method comprising:
    relatively moving the emitter and the packaging material to produce a flow of a gaseous medium that enters a gap between the emitter and the packaging material;
    controlling a movement profile between the emitter and the packaging material; and
    sterilizing, by the at least one cloud, the entire flow of the gaseous medium that enters the gap between the emitter and the packaging material by adjusting the movement profile.

2. Method according to claim 1, wherein the packaging material is tube-shaped packaging material possessing an opening that opens into an interior of the tube-shaped packaging material, and wherein the emitter is operated to sterilize at least the interior of the tube-shaped packaging material through the opening of the tube-shaped packaging material.

3. Method according to claim 2, comprising performing mutual relative movement between the emitter and the tube-shaped packaging material, during which mutual relative movement a portion of the emitter is temporarily inserted through the opening of the tube-shaped packaging material to sterilize the interior of the packaging material.

4. Method according to claim 3,
wherein the tube-shaped packaging material extends along an axis,
the method comprising
providing a cloud large enough to at least cover an inner cross section of the tube-shaped packaging material, said inner cross section being perpendicular to the axis, and
adjusting the movement profile such that the cloud forms an aseptic barrier in the tube-shaped packaging material that sterilizes any inflow of the gaseous medium between the emitter and the tube-shaped packaging material before the gaseous medium reaches a sterilized interior of the tube-shaped packaging material.

5. Method according to claim 3, comprising:
inserting the emitter into the tube-shaped packaging material to create an outflow of the medium out of the tube-shaped packaging material through the opening,
pulling the emitter out of the tube-shaped packaging material to create an inflow of the medium into the tube shaped packaging material, and
adapting an inflow-speed and an outflow-speed of the medium using the movement profile.

6. Method according to claim 5, wherein the movement profile comprises at least a first position at which the emitter and the opening of the tube shaped packaging material are on a common level, and a second position at which the emitter is located in the interior of the tube-shaped packaging material, the method comprising:
adjusting the movement profile so that a time span for moving from the first position to the second position, defined as run-in, is shorter than a time span for moving from the second position to the first position, defined as run-out.

7. Method according to claim 5, wherein the movement profile comprises at least a first position and a second position, the emitter comprising an electron exit window, the method comprising:
positioning the electron exit window of the emitter and the opening of the tube-shaped packaging material at a common level at the first position of the movement profile,
positioning the electron exit window of the emitter in the interior of the of the tube-shaped packaging material at the second position of the movement profile,
adjusting the movement profile so that a time span for moving from the first position to the second position is shorter than a time span for moving from the second position to the first position.

8. Method according to claim 3, comprising pulling the emitter out of the tube-shaped packaging material to create an inflow of the medium into the tube-shaped packaging material, and
adapting an inflow-speed of the medium, using the movement profile, such that the inflow of the medium into the tube-shaped packaging material is sterilized by the cloud, the cloud thereby forming an aseptic barrier.

9. Method according to claim 2, comprising:
creating overpressure in the interior of the tube shaped packaging material to prevent inflow of the medium from coming into the tube shaped packaging material.

10. Method according to claim 1, wherein the tube-shaped packaging material extends along an axis,
wherein the cloud possesses a width that extends perpendicular to the axis, and
wherein the cloud possesses a length that extends along the axis,
the method comprising:
providing a power supply configured to influence the width and the length of the cloud; and
operating the power supply so that the width of the cloud covers at least an area between the emitter and the packaging material.

11. Method according to claim 10, comprising:
adapting the length and/or the width of the cloud during run-out when the emitter is outside the packaging material to cover the opening of the packaging material with the cloud.

12. Method according to claim 11, comprising:
lowering and/or stopping a speed of the run-out when the emitter is above the opening; and
sterilizing the inflow of the medium.

13. Method according to claim 1, comprising:
adapting an energy level of the charge carriers and/or a dose rate of the emitter as a function of a flow-speed of the medium in between the emitter and the packaging material.

14. Method according to claim 1, wherein the method comprises:
moving the packaging material along the axis through operation of drive unit to produce the movement profile.

15. Device for sterilizing packaging material, comprising:
an emitter configured to emit charge carriers forming at least one cloud,
the emitter and the packaging material being movable relative to each other so that a flow of a gaseous medium enters a gap between the emitter and the packaging material,
a control unit configured to control a movement profile between the emitter and the packaging material to sterilize the entire flow of the gaseous medium that enters the gap between the emitter and the packaging material by the at least one cloud, by adjusting the movement profile.

16. Method for sterilizing packaging material through use of an emitter that is adapted to emit charge carriers forming at least one cloud, the packaging material being a tube-shaped packaging material possessing an opening that opens into an interior of the tube-shaped packaging material, the method comprising:
relatively moving the emitter and the tube-shaped packaging material to temporarily introduce a portion of the emitter into the interior of the tube-shaped packaging material by way of the opening of the tube-shaped packaging material and emitting the charge carriers into the interior of the tube-shaped packaging material to sterilize the interior of the tube-shaped packaging material;
relatively moving the emitter and the tube-shaped packaging material to remove the emitter from the interior of the tube-shaped packaging material and also create an inflow of gaseous medium into the interior of the tube-shaped packaging material, the gaseous medium being different from the charge carriers;
controlling a movement profile between the emitter and the tube-shaped packaging material;
sterilizing, by the at least one cloud, the inflow of the gaseous medium into the interior of the tube-shaped packaging material by adapting an inflow-speed of the gaseous medium using the movement profile, the cloud thereby forming an aseptic barrier.

17. Method according to claim 16, wherein the relatively moving the emitter and the tube-shaped packaging material to remove the emitter from the interior of the tube-shaped packaging material includes moving the emitter relative to the tube-shaped packaging material.

* * * * *